United States Patent [19]

Durlach

[11] 4,271,189

[45] Jun. 2, 1981

[54] LITHIUM DERIVATIVES OF TAURINE HAVING REINFORCED NEURO-MUSCULAR ACTIVITY

[75] Inventor: Jean P. Durlach, Paris, France

[73] Assignee: Les Laboratoires Meram, Paris, France

[21] Appl. No.: 103,729

[22] Filed: Dec. 14, 1979

Related U.S. Application Data

[63] Continuation-in-part of Ser. No. 888,202, Mar. 20, 1978, Pat. No. 4,199,601.

[30] Foreign Application Priority Data

Mar. 23, 1977 [FR] France ................................. 77 08692

[51] Int. Cl.³ ................. C07C 143/155; A61K 31/195
[52] U.S. Cl. ................................ 424/315; 260/513 N
[58] Field of Search ..................... 260/513 N; 424/315

[56] References Cited

U.S. PATENT DOCUMENTS

| 3,232,968 | 2/1966 | Schenck et al. | 260/513 N |
| 3,344,174 | 9/1967 | Broussalian | 260/513 N |
| 3,544,597 | 12/1970 | Killam | 260/513 N |
| 3,960,918 | 6/1976 | Schroeck | 260/513 N |

FOREIGN PATENT DOCUMENTS 1090779  11/1967  United Kingdom ................ 260/513 N

OTHER PUBLICATIONS

Teraoka, "Hoppe–Seyler Zeitscrift fur Physiologische Chemie," 145 242 (1925).

*Primary Examiner*—Joseph E. Evans
*Attorney, Agent, or Firm*—Lewis H. Eslinger

[57] ABSTRACT

The present invention relates to derivatives of taurine represented by the general formula:

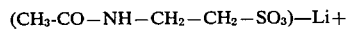

to the process for preparation thereof from taurine and to application thereof as drugs having a reinforced neuro-muscular activity.

6 Claims, No Drawings

LITHIUM DERIVATIVES OF TAURINE HAVING REINFORCED NEURO-MUSCULAR ACTIVITY

This application is a continuation-in-part of copending application Ser. No. 888,202, filed Mar. 20, 1978 now U.S. Pat. No. 4,199,601.

The invention relates to new derivatives of taurine having a reinforced neuro-muscular activity and to use thereof as drugs.

The compounds according to the invention are represented by the general formula:

$$(CH_3-CO-NH-CH_2-CH_2-SO_3)_n{}^- M^+$$

in which M represents an alkali-metal or alkaline-earth metal, of valency n, n being equal to 1 or 2, or the quaternary ammonium cation of a nitrogenous organic base.

The cations represented in the above formula by $M^+$ are preferably those which give the compounds according to the invention reinforced neuro-muscular properties: i.e. for example lithium, caesium, rubidium, calcium, magnesium, among the alkali- or alkaline-earth metals, or zinc, and, among the nitrogenous organic bases, pyridoxine, ajmaline, sparteine, etc.

The salts of N-acetyl taurine present new properties over taurine, and in particular an increased power of cellular penetration, this in particular increasing the neuro-muscular activities of this sulfonic aminoacid. In fact, N-acetylation allows an increase in the cellular penetration of various other sulphured organic compounds: penicillamine, homocysteine or its thiolactone for example, without altering the biological activity thereof. Now, although taurine exerts major physiological effects on the nervous system which are considerable enough to class this aminoacid among the neuro-mediators or neuro-modulators, these effects can be observed in practice only by the administration "in situ" of the aminoacid.

On the other hand, N-acetylation, a conventional process of detoxification, effectively reduces the toxicity of certain of these sulphured compounds like, moreover, cysteamine.

Among the metal salts according to the invention, that of potassium is interesting as the taurine acts on the permeability of the membrane by maintaining this ion in the cell; those of lithium, caesium and rubidium exert central nervous effects enabling the neuroleptic effects of the taurine to be increased; the salts of magnesium and calcium act on the stability of the membrane.

Among the organic salts according to the invention, pyridoxine occurs at various essential stages of the metabolism of the taurine and the various organic bases which have been fixed on the acetyltaurine enable their complementary and additive pharmacodynamic properties to be added thereto.

The salts according to the invention are generally prepared by a process similar to the process for the preparation of the acetyltaurinate of sodium by: M. TERAOKA; Hoppe-Seyler Zeitschrift für Physiologische Chemie 145 242 (1925); i.e. by action of acetic anhydride on the taurine in the presence of the base corresponding to the salt which it is desired to obtain, at the boiling temperature of the mixture.

The examples given hereinbelow illustrate the process for preparation of the compounds according to the invention.

EXAMPLE 1

Preparation of N-acetyl-taurinate of sodium $$CH_3-CO-NH-CH_2-CH_2-SO_3Na$$

In the three-necked, 4-liter flask, 1.5 liters of water then 64 g of sodium hydroxide are introduced with stirring; after dissolution, 200 g of pure taurine are then introduced all at once. 1 liter of acetic anhydride is then poured through the bromine funnel so that the temperature does not exceed 70° C. Heating is then effected for 2 hours to reflux and concentration is effected in vacuo to a maximum. The liquid residue is transvased into a procelain vat and is dried in vacuo for 4 hours at 100° C. The solid obtained is ground and the fine powder is rendered pasty once in 1 liter of acetone and once in 1 liter of methanol. Oven-drying is effected. Whitish-cream crystals are obtained.

Yield: 66%

| Analysis: | Calculated (%) | Found (%) |
|---|---|---|
| Na | 12.17 | 12.21 |
| N | 7.40 | 7.51 |

EXAMPLE 2

Preparation of N-acetyl-taurinate of potassium $$CH_3-CO-NH-CH_2-CH_2-SO_3K$$

In a flask equipped with magnetic stirring means, are introduced 5 g of taurine, 3 g of potash in solution in 80 g of water and 25 ml of acetic anhydride which are added slowly. The temperature rises to 40° C. Heating is then effected for 2 hours to reflux (90° C.). The mixture is completely concentrated in vacuo and the residue is recrystallized twice in 500 ml of 95% ethyl alcohol and rendered pasty in 200 ml of hot methanol, then dried. 7 g of a white solid is obtained.

M.P. 212° C. Yield: 60%

| Analysis: | Calculated (%) | Found (%) |
|---|---|---|
| C | 23.41 | 23.42 |
| H | 3.93 | 4.02 |
| N | 6.83 | 7.08 |
| K | 19.02 | 19.11 |

EXAMPLE 3

Preparation of N-acetyl-taurinate of lithium $$CH_3-CO-NH-CH_2-CH_2-SO_3Li$$

5 g of taurine and 3.4 g of lithia are mixed with stirring in 50 ml of water. 30 ml of acetic anhydride are then rapidly introduced, heating is effected for 1 hour to reflux, complete concentration is effected in vacuo, the residue is recrystallized in a dilute alcoholic mixture. Whitish-cream crystals are obtained.

Yield: 70%

| Analysis: | Calculated (%) | Found (%) |
|---|---|---|
| Li | 4.04 | 4.31 |
| N | 8.09 | 8.21 |

| Analysis: | Calculated (%) | Found (%) |
|---|---|---|
| Dosage per HClO₄: 99% | | |

EXAMPLE 4

Preparation of N-acetyl-taurinate of magnesium

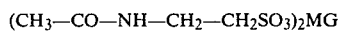

(CH₃—CO—NH—CH₂—CH₂SO₃)₂MG 10 g of pure magnesia and 150 ml of water then 15 g of taurine and, finally, 150 ml of acetic anhydride are introduced. The mixture is taken to reflux for one hour, concentrated in vacuo to a maximum, the solid is dried in vacuo at 100° C. for 24 hours and is rendered pasty in 200 ml dry and hot methanol. White crystals are obtained.

Yield: 65%

| Analysis: | Calculated (%) | Found (%) |
|---|---|---|
| Mg | 6.73 | 6.94 |
| N | 3.93 | 3.81 |
| Dosage per EDTA : 102% | | |

EXAMPLE 5

Preparation of N-acetyl-taurinate of calcium

(CH₃—CO—NH—CH₂—CH₂SO₃)₂Ca

In a three-necked 500 ml-flask are introduced 50 g of permuted water, 25 g of taurine and 10 g of calcium carbonate. Heating is effected to 100° C. and is then stopped. 60 ml of acetic anhydride are poured so as to maintain a slight reflux. At the end of pouring, heating is effected for 2 hours to 105° C., the mixture is concentrated to dryness, oven-drying is effected in vacuo for 16 hours at 120° C. The residue is rendered pasty in 50 ml of acetic acid, filtered and washed 3 times in 50 g of acetone; it is dried and 17 g of a white, 98% pure solid is obtained, the melting point of which is higher than 250° C.

The acute toxicity of the compounds according to the invention was studied by the intraperitoneal route in the male mouse. The results obtained were as follows:

The LD₅₀ by the intraperitoneal route in the male mouse is 3234 mg/kg for N-acetyltaurinate of potassium; 3875 mg/kg for the N-acetyltaurinate of lithium; 1604 mg/kg for the N-acetyltaurinate of calcium 1709 mg/kg for the N-acetyltaurinate of magnesium.

The LD₅₀ by the oral route in the male mouse is 8170 mg/kg for the N-acetyltaurinate of potassium; 6630 mg/kg for the N-acetyl-taurinate of lithium; 13230 mg/kg for the N-acetyltaurinate of calcium; 17400 mg/kg for the N-acetyltaurinate of magnesium.

The products of Examples 2, 3 and 4 have been the subject of a pharmacological study and their neuro-muscular activity has been demonstrated by the following six tests, according to which the taurine proved to be without any activity:

1. The investigation behaviour of the mouse was studied by the "Holed board" test (Boissier and Simon; Arch. Int. Pharmacodyn. 1964, 147, 3–4), 2. The study of the spontaneous motility of the mouse was made by using Boissier's photoelectric actimeter.

3. The study of the motility of the mice was also made by using Boissier's photoelectric actimeter, after amphetamine-acetyl-taurinate interaction according to the invention: the mice are treated simultaneously with 10 mg/kg (IP) of dextrorotatory amphetamine and with an optimal dose of acetyltaurinate.

4. A study of the hypothermia in the mouse was effected by determining the rectal temperature of the mice 30 mins. before the intraperitoneal administration of the product, at the moment of this administration, then 30 mins., 1 hour, 2, 3 and 4 hrs. after the injection of the product.

5. The study of the hypothermia after amphetamine-acetyl-taurinate interaction according to the invention was made according to the same method as previously in the mouse, the animals being treated simultaneously with 30 mg/kg (IP) of dextrorotatory amphetamine and with an optimal dose of the product to be tested.

6. A test was also made of the appetite- and thirst-depressant activities in the rat.

The results of the pharmacological study are as follows:

The N-acetyl-taurinate of lithium provokes in the mouse a very clear increase in the investigation behaviour and in the motility in free condition; an increase in the motive agitation and an increase in the amphetaminic excitation. It also provokes in the mouse a significant hypothermia which is completely eliminated by the injection of amphetamine simultaneously with the product; in the rat, it provokes very clear appetite- and thirst-depressant actions (very substantial reduction in the taking of food and drink consumed).

The value of lithium salts in the treatment of depressions and in particular of manic-depressive psychosis, is well-known. But the major disadvantage of this therapy resides in the toxicity of the currently known salts (carbonate, citrate, gluconate). The study of acute toxicity in male mice, by intraperitoneal and oral routes, has shown that lithium N-acetyltaurinate had a clearly reduced acute toxicity compared with that of lithium carbonate, as shown in the following Table wherein the DL50 are expressed in mg of lithium per Kg.

| | LD₅₀ IN THE MALE MOUSE | |
|---|---|---|
| | Oral route | Intraperitoneal route |
| Lithium carbonate | 162 mg/Kg | 88 mg/Kg |
| N-acetyltaurinate of lithium | 266 mg/Kg | 155 mg/Kg |

This reduction of acute toxicity was confirmed by the evaluation of the minimum lethal dose by intraveinous route in male rabbits, comparatively beween lithium citrate and lithium N-acetyltaurinate:

In the same experimental conditions, the minimum lethal dose is 42 mg of lithium with lithium citrate, and 204 mg lithium with lithium N-acetyltaurinate.

A study of the chronic toxicity in rats was conducted comparatively between lithium N-acetyltaurinate and lithium carbonate:

For three months, rats received doses of 8 mg/Kg and 24 mg/Kg per day of lithium, first in the form or lithium carbonate, and in the form of lithium N-acetyl-taurinate.

The histological study has shown that tubular renal lesions appear in all the treated animals. However, thirty days after the treatment has stopped, a reversion of the lesions is noted in all the animals treated with lithium acetyltaurinate, whereas the lesions persist in the animals treated with lithium carbonate at the dose of 24 mg of lithium per Kg.

In conclusion, the lithium N-acetyltaurinate has proved less toxic with respect to lithium carbonate, not only from the point of view of acute toxicity, but also from the point of view of chronic renal toxicity which up to now did constitute one of the major dangers of lithiotherapy.

Furthermore, the neuro-muscular activity of the lithium N-acetyltaurinate has been evaluated in comparison with that of taurine and of the other salts of N-acetyltaurine, using the test of morphinic agitation. This test is described by CAROLL and SHARP (Science 1971, 172, June 25, "Rubidium and lithium: opposite effect on amine mediated excitement"). It consists in measuring the agitation (or spontaneous motility) started off in mice by intra-peritoneal injection of 25 mg/Kg of morphine sulphate, and the effect on said agitation of a preliminary 5-day treatment with the compound under study, at doses of 100, 500 and 2500 mg/Kg per os, the test with the morphine sulphate being carried out 30 mins. after the compound has been administered on the 5th day.

The results were as follows:

In small doses (100 mg/Kg) the lithium acetyltaurinate potentiates the morphinic agitation (by 45% between the 75th and the 90th minute), an effect comparable to that of lithium gluconate whereas at stronger doses (500 and 2500 mg/Kg) there is an antagonistic effect on the agitation caused by the morphine sulphate (see Table hereunder).

Thus the lithium acetyltaurinate has a biphasic effect according to the test of the morphinic agitation, which differentiates it from taurine which has no effect, and from the other acetyltaurine salts (Mg and Ca salts for example) which have a mono-phasic effect, antagonistic to the morphinic agitation even in small doses.

Therefore, the lithium N-acetyltaurinate can be used in all therapeutic prescriptions of lithium salts and in particular for the treatment of manic-depressive psychosis, because it has an increased neuro-muscular activity, without any of the dangers of acute and chronic toxicity found with the other known lithium salts.

| % VARIATION OF MOTILITY WITH RESPECT TO MORPHINE CONTROLS (25 mg/kg IP) | | | |
|---|---|---|---|
| TIME | ATA-Li* 100 mg/kg PO | ATA-Li 500 mg/kg PO | ATA-Li 2500 mg/kg PO |
| 0–15 mins. | + 39.1 | − 59.6** | − 21.4 |
| 15–30 mins. | + 46.3 | − 64.3** | − 41.6 |
| 30–45 mins. | + 43.1 | − 62** | − 59.9** |
| 45–60 mins. | + 39.4 | − 62.3** | − 58.8** |
| 60–75 mins. | + 60.5 | − 57.8 | − 47.2 NS |
| 75–90 mins. | + 93.3 | − 53.8 | − 58.6* |
| 90–105 mins. | + 34.5 | − 57.4 | − 70 ** |
| 105–120 mins. | — | − 40 | − 54 |

*ATA Li = N-acetyltaurinate de lithium

The N-acetyl-taurinate of potassium provokes an increase in the investigation behaviour in the mouse, not proportional to the dose, a slight increase in the motive agitation and a reduction in the amphetaminic excitation.

The N-acetyl-taurinate of magnesium provokes in the mouse an increase in the motive agitation at a low dose (100 mg/kg) and, on the contrary, a very clear reduction of this agitation at high dose (200 mg/kg). It also provokes a reduction in the amphetaminic excitation and a very considerable reduction in the maximum rectal temperature, 2 hours after the injection of the product, this action being completely eliminated by simultaneous injection of amphetamine, 1 hour after the injection.

The N-acetyltaurinate of calcium provokes, in the mouse, a reduction in the motive agitation at a low dose (100 mg/kg), an increase in the exploratory activity, a significant reduction in the rectal temperature; on the other hand, it does not modify either the amphetaminic excitation nor hyperthermia.

For use in human therapy, the compounds according to the invention may be presented in the following forms of administration:

by the oral route, such as tablets, sugar-coated pills, capsules, gelatin-coated capsules, solutions, containing the active product at the unitary dose of 0.30 to 1 g and, for the solutions, from 0.5 to 5 g per 10 ml, the dose to be administered daily being from 0.30 and 10 g and preferably from 1.5 to 2 g;

by the parenteral route, such as injectable solutions packaged in ampoules, containing from 0.5 to 5 g of active product per ampoule;

by the topical route, such as lotions, creams, ointments.

The compounds according to the invention are used for treating neuro-muscular affections.

The N-acetyl taurinate of potassium may be used as musculo-myocardium stimulant, particularly in arterites. The N-acetyl taurinate of magnesium is useful in all indications in magnesium-therapy, particularly as neurosedative and in epilepsy, and as tissue protector, particularly antianoxic and antiaggregant.

The N-acetyl-taurinate of calcium is useful in all indications in calcium-therapy, in particular as neurosedative and drug treating fatigue.

The N-acetyl-taurinate of lithium may be used in all indications of lithium, with less danger of toxic accidents and an increased neurotropic activity.

The following observation is given by way of example: Mr. Andre V., aged 32 years, has been treated for 7 years for a neuromuscular hyperexcitability, with a wide range of neuro-vegetative disorders. He presents critical phenomena of lipothymia type, anxious crises with paroxysmal tachycardia. He has had four grand mal epileptic crises.

The electroencephalogram shows slow waves, the ionic balance is normal except for a discrete reduction (51 mg/liter) of the erythrocyte magnesium.

Earlier treatments associating phenobarbital, β-blocking agents, various types of oral magnesium therapy, have given partial results. A treatment by the N-acetyl taurinate of magnesium associating, the first ten days, a venous perfusion in isotonic serum with glucose added of 1 g at the regular daily dose of 1.5 g per os (three doses of 0.5 g) brings a complete recovery of the general state with, in particular, disappearance of the critical phenomena, verified with a recession of 13 months. Mr. Mon . . . S, aged 34 years, bipolar manic-depressive psychosis with predominating depressive phase and passage into manic phase helped by the use of tricyclic drugs. 2 suicide attempts. Predominance of psychomotive inhibition. Treatment with lithium carbonate (1 g/day) has not permitted to obtain a lithemia greater than 0.5 meq/liter; on the contrary, an increase to 1.5 mg per day has permitted to obtain a lithemia varying from 0.8 meq/liter to 1.30 meq/liter. Signs of intolerance unexpectedly appear, apart from permanent tremblings: nauseas, vomitings, hypotension, etc... On the contary, a stability of the mood is obtained. Substitution for lithium carbonate of the same weight dose (1.5 g/day) of ATA Li (i.e., a clearly lower dose of lithium) permits the suppression of all toxic signs with a lithemia between 0.5 and 0.6 meq, and brings the same stability of the mood as the subtoxic dose of lithium carbonate. Mrs. Ken . . . E, aged 37 years, suffering from chronic alcoholism and having presented two attacks of predelirium (rumfits), the chronic intoxication corresponding to a daily intake of 1.5 liter of wine and a variable intake of aperitifs and of liquors. Besides permanent tremblings and facial erythrosis, she has had on two occasions attacks of mental aberration with agitation, hallucinations and on the second occasion, convulsions. During this second attack, venous perfusion in isotonic serum with glucose of 1 g of ATA Ca per hour for three hours (total dose 3 g/24 hrs.) has brought a sedation of the attack with a state of euphoria. Acceptance by the patient of a daily intake of 1.5 g of ATA Ca (3 tablets of 0.5 g daily) has considerably reduced the tremblings, improved the intellectual efficiency and upkept the alcoholic weaning.

What is claimed is:

1. A derivative of taurine represented by the formula:

$$(CH_3-CO-NH-CH_2-CH_2-SO_3)^- Li^+.$$

2. A compound according to claim 1 used as drugs, in particular as agents having a reinforced neuromuscular activity.

3. Pharmaceutical compositions containing as active ingredient a compound according to claim 1 associated with a suitable excipient for administration by the oral, parenteral or local route.

4. Orally administered forms of the compositions according to claim 3, containing the active ingredient at the unitary dose of 0.30 g to 1 g for capsules, sugar-coated pills, tablets, gelatin-coated capsules, and from 3 to 5 g/10 ml for the solutions.

5. Parenterally administered forms of the compositions according to claim 4, containing the active ingredient at a dose of 0.5 to 2 g per injectable ampoule.

6. A method of treating manic-depressive psychosis by administering an effective amount of a compound as recited in claim 1.

* * * * *